United States Patent [19]

Engelhardt et al.

[11] Patent Number: 5,068,298

[45] Date of Patent: * Nov. 26, 1991

[54] ALKENYL-PHOSPHONIC AND -PHOSPHINIC ESTERS, PROCESS FOR THEIR PREPARATION, THEIR USE AND HYDROGELS PREPARED USING THEM

[75] Inventors: Friedrich Engelhardt; Ulrich Riegel, both of Frankfurt am Main; Joachim Gersdorf, Wiesbaden; Hans-Jerg Kleiner, Kronberg, all of Fed. Rep. of Germany

[73] Assignee: Cassella Aktiengesellschaft, Frankfurt am Main, Fed. Rep. of Germany

[ * ] Notice: The portion of the term of this patent subsequent to Nov. 19, 2008 has been disclaimed.

[21] Appl. No.: 542,763

[22] Filed: Jun. 25, 1990

[30] Foreign Application Priority Data

Jul. 7, 1989 [DE] Fed. Rep. of Germany ....... 3922327

[51] Int. Cl.$^5$ .................... C08F 230/04; C08F 230/02
[52] U.S. Cl. ..................... 526/240; 526/278; 524/547; 524/807; 524/916
[58] Field of Search .............. 526/278, 240; 524/547, 524/807, 916; 558/161, 164, 165; 549/221

[56] References Cited

U.S. PATENT DOCUMENTS

| | | | |
|---|---|---|---|
| 3,163,627 | 12/1964 | Craver | 525/37 |
| 3,641,202 | 2/1972 | Biranowski | 525/37 |
| 4,959,441 | 9/1990 | Engelhardt | 558/161 |
| 4,977,066 | 12/1990 | Gersdorf | 430/277 |

FOREIGN PATENT DOCUMENTS 1243192 6/1967 Fed. Rep. of Germany .

*Primary Examiner*—Joseph L. Schofer
*Assistant Examiner*—M. Nagumo
*Attorney, Agent, or Firm*—Connolly and Hutz

[57] ABSTRACT

The present invention relates to compounds of the general formula I

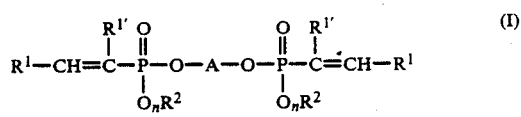

in which
$R^1$, $R^{1'}$, $R^2$, A and n are as defined in the description, a process for their preparation, their use and also hydrogels prepared using them.

4 Claims, No Drawings

ALKENYL-PHOSPHONIC AND -PHOSPHINIC ESTERS, PROCESS FOR THEIR PREPARATION, THEIR USE AND HYDROGELS PREPARED USING THEM

The invention relates to novel alkenyl-phosphonic and -phosphinic esters of polyhydric alcohols, a process for their preparation, their use and hydrogels prepared using them.

The preparation of hydrogels in aqueous solution is normally carried out using, as cross-linking agents, compounds such as bis-acrylamidoacetic acid, trimethylolpropane triacrylate, tetraallyloxyethane or the like.

Moreover, the German Patent Application P 38 17 425-1 describes alkenyl-phosphonic and -phosphinic esters of 1,1,1-tris(hydroxymethyl)alkanes and of 2,2-bis-hydroxymethyl-1,3-propanediol.

The object of the present invention is to provide novel water-soluble, polymerizable compounds which act as cross-linking agents and by the use of which hydrogels are obtained having improved properties with regard to gel strength and water retention.

Surprisingly, this object is achieved using the compounds of the general formula I

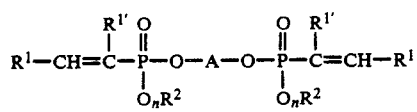

in which
R¹ and R¹', independently of one another, are hydrogen or $(C_1-C_4)$-alkyl,
R² is $(C_1-C_4)$-alkyl,
n is 0 or 1 and
A is straight-chain or branched $(C_2-C_{12})$-alkylene or a group of the formula II

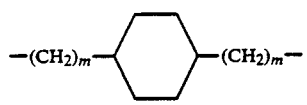

in which m is 0 or 1, or a group of the formula III

in which $R^3$ and $R^4$, independently of one another, are $(C_1-C_4)$alkyl and p is 0 or 1 or a group of the formula IV

in which x is 1 to 12 or a group of the formula V

in which x is 1 to 12 or a group of the formula VI

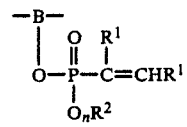

in which B represents straight-chain or branched $(C_3-C_{12})$-alkylene and $R^1$, $R^{1'}$, $R^2$ and n are as defined above.

$R^1$ and $R^{1'}$ are preferably hydrogen or methyl
$R^2$ is preferably methyl, ethyl or propyl.

If A or B are represented by an alkylene group, this preferably has 3 to 8 carbon atoms.

In the group of the formula III, $R^3$ and $R^4$ are preferably methyl and ethyl.

In the groups of the formulae IV and V, x preferably represents 1 to 4.

A preferably represents 1,3-propylene, 1,4-butylene, 1,6-hexylene, 2,5-hexylene, 2,2-dimethyl-1,3-propylene, 1,4-cyclohexylene, 2-methyl-2,4-pentenyl and also the radicals derived from diethylene glycol, triethylene glycol and dipropylene glycol.

The compounds according to the invention of the general formula I can be prepared by reacting an alkenylchlorophosphonic ester of the general formula VII

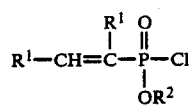

or an alkenylphosphinoyl chloride of the general formula VIII

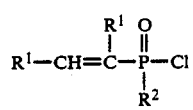

in which $R^1$, $R^{1'}$ and $R^2$ are as defined above, with an alcohol of the general formula IX

or with an alcohol of the general formula X

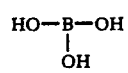

in which A and B are as defined above.

The hydrogen chloride released during the reaction is bound, preferably by using a suitable tertiary amine as an acid acceptor.

Examples of suitable tertiary amines are trialkylamines having 1 to 4 carbon atoms per alkyl radical such as, for example, triethylamine, dialkylanilines having 1 to 4 carbon atoms in the alkyl radical such as, for example, N,N'-dimethylaniline, and pyridine.

The reactions are preferably carried out using mole ratios of organophosphorus compound : acid acceptor : alcohol of the general formula IX of 2:2:1 or using mole ratios of organophosphorus compound : acid acceptor : alcohol of the general formula X of 3:3:1.

The reactions are preferably carried out with cooling at −10° to +40° C. in suitable inert solvents.

Examples of suitable inert solvents are halogenated hydrocarbons such as, for example, methylene chloride, aromatic hydrocarbons such as, for example, toluene, ethers, such as, for example, tetrahydrofuran, or aliphatic nitriles such as, for example, acetonitrile.

The products resulting from the abovementioned processes may in some cases be purified by distillation under a high vacuum, in particular with the aid of a thin-film evaporator. However, in some cases they may also be further processed directly in the form of the crude product.

The alcohols of the general formulae IX and X are known and are commercially available or can be prepared by known methods. Examples of dihydric alcohols of the general formula IX are 1,3-propanediol, 1,4-butanediol, 1,6-hexanediol, 2,5-hexanediol, 2,2-dimethyl-1,3-propanediol, 2-methyl-2,4-pentanediol, cyclohexane-1,4-diol, diethylene glycol, triethylene glycol and dipropylene glycol.

Alcohols of the general formula IX which introduce a group of the formula III into the compounds according to the invention are described, for example, in DE 1,151,813. Examples of trihydric alcohols of the general formula X are glycerol and 1,2,6-hexanetriol.

The organophosphorus compounds of the general formulae VII and VIII can be obtained commercially or by well known methods (for example, Houben-Weyl, Methoden der Organischen Chemie, published by Georg Thieme Verlag, Stuttgart, Vol. 12/1, 1963 pages 217 et seq. and 338 et sec.).

Preference is given to ethyl vinylchlorophosphonate as a compound of the general formula VII, and to methylvinylphosphinoyl chloride as a compound of the general formula VIII.

The compounds according to the invention of the general formula I are used as so-called cross-linking agents, i.e. as polymerizable polyunsaturated monomers, in the synthesis of polymers, in particular of water-swellable hydrogels made from unsaturated monomers. In these uses, a significant advantage of the said compounds is their very good solubility not only in polar but also in non-polar solvents. Thus, in contrast to trimethylolpropane triacrylate or trimethylolpropane trimethacrylate, the compounds of the general formula I are miscible in any proportions with water. Moreover, the said substances have low volatility and low odour. These properties give the further advantage of a significantly reduced tendency to diffuse or evaporate during the polymerization process.

The present invention also provides water-swellable hydrogels which can be prepared by copolymerization of hydrophilic monomers and are characterized in that the copolymerization employs compounds of the general formula I as crosslinking agents.

Suitable hydrophilic monomers are, in particular, acrylic acid, methacrylic acid, crotonic acid, 2-acrylamido-2-methylpropanesulphonic acid and -phosphonic acid, vinylphosphonic acid, semiesters of vinylphosphonic acid, salts thereof, acrylamide, N-vinylamides, or mixtures thereof. Preference is given to acrylic acid and salts thereof.

The compounds of the general formula I are preferably used in amounts of from 0.05 to 20% by weight, relative to the total weight of monomers.

The polymerization can be carried out in homogeneous phase, for example in aqueous solution as so-called gel polymerization, or by the process of inverse emulsion polymerization. A further method for the synthesis of the hydrogels according to the invention is precipitation polymerization from organic solvents such as, for example, alcohols, preferably tert-butanol, or hydrocarbons such as hexane or cyclohexane.

The polymerization can be initiated using free-radical formers such as, for example, organic or inorganic peroxides and azo compounds. Examples of these are benzoyl peroxide, tert-butyl hydroperoxide, cumyl hydroperoxide $(NH_4)_2S_2O_8$, $K_2S_2O_8$, $H_2O_2$ or azodiisobutyronitrile. Redox systems are also eminently suitable as polymerization initiators.

Finally, the polymerization may also be initiated by high-energy radiation.

The hydrogels according to the invention are eminently suitable as absorbents of aqueous liquids and for the formulation of cosmetic preparations.

Copolymers made from acrylic acid and the compounds according to the invention of the general formula I have particularly advantageous characteristics as super absorbing polymers (SAPs) when employed in sanitary articles such as, for example, diapers, it being possible for some of the acrylic acid to be present in the form of the alkali metal salt or ammonium salt. The neutralization can be carried out both before and after polymerization.

In contrast to the prior-art compounds, the water-swellable hydrogels according to the invention have a more homogenous network structure, since the compounds according to the invention of the general formula I are not only completely soluble in water but also in polar organic solvents. As a result, hydrogels have not only a high gel strength but also high absorption capacities.

The present invention is described, with regard to the compounds of the general formula I, by the Examples 1 to 9 which follow and, with regard to the hydrogels, by the Examples 10 to 30.

EXAMPLE 1

Reaction of methyl-vinylphosphinoyl chloride with 1,4-butanediol 36 g (0.4 mol) of 1,4-butanediol were added, together with 81 g (0.8 mol) of triethylamine, to 270 ml of toluene. To this were added dropwise with vigorous stirring 99.6 g (0.8 mol) of methyl-vinylphosphinoyl chloride at 20°-25° C. with cooling. Stirring was then continued for 20 hours and then the triethylamine hydrochloride which had been formed was filtered off under suction. The precipitate was washed with toluene and the filtrate was freed from toluene by distillation in vacuo. This residue was distilled at 0.093 kPa and at a bath temperature of 190° C. via a thin-film evaporator. This gave 92 g. $n_D^{20}$: 1.4805. The yield was 87% of theory. $C_{10}H_{20}O_4P_2$ (266)

| Calc.: | 45.11% C | 7.52% H | 23.31% P |
|---|---|---|---|
| Found: | 45.1% C | 7.4% H | 22.9% P |

EXAMPLE 2

Reaction of methyl-vinylphosphinoyl chloride with 1,6-hexanediol 59.1 g (0.5 mol) of 1,6-hexanediol were added, together with 101 g (1.0 mol) of triethylamine, to 200 ml of toluene. To this were added dropwise with vigorous stirring 124.5 g (1.0 mol) of methyl-vinylphosphinoyl chloride at 20° C. with cooling. Stirring was then continued for 18 hours and then the triethylamine hydrochloride which had been formed was filtered off under suction. The precipitate was washed with toluene and the filtrate was freed from toluene by distillation in vacuo. This residue was distilled at 0.067 kPa and at a bath temperature of 205° C. via a thin-film evaporator. This gave 135 g. $n_D^{20}$: 1.4819 The yield was 92% of theory. $C_{12}H_{24}O_4P_2$ (294)

| Calc.: | 48.98% C | 8.16% H | 21.09% P |
|---|---|---|---|
| Found: | 48.9% C | 8.3% H | 21.0% P |

EXAMPLE 3

Reaction of methyl-vinylphosphinoyl chloride with 2,5-hexanediol 59.1 g (0.5 mol) of 2,5-hexanediol were added, together with 101 g (1.0 mol) of triethylamine, to 200 ml of toluene. To this was added dropwise with vigorous stirring 124.5 g (1 mol) of methyl-vinylphosphinoyl chloride at 20° C. with cooling. Stirring was then continued for 18 hours and then the triethylamine hydrochloride which had been formed was filtered off under suction. The precipitate was washed with toluene and the filtrate was freed from toluene by distillation in vacuo. This residue was distilled at 0.2 kPa and at a bath temperature of 200° C. via a thin-film evaporator. This gave 130 g. The resulting product had an acid number of 44. It was a crude product. The yield was 92% of theory. $C_{12}H_{24}O_4P_2$ (294)

EXAMPLE 4

Reaction of methyl-vinylphosphinoyl chloride with 2,2-dimethyl-1,3-propanediol 15.6 g (0.15 mol) of 2,2-dimethyl-1,3-propanediol were added, together with 30.4 g (0.3 mol) of triethylamine, to 75 ml of toluene. To this was added dropwise with vigorous stirring 37.35 g (0.3 mol) of methyl-vinylphosphinoyl chloride at 20°-25° C. with cooling. Stirring was then continued followed by filtering off under suction the triethylamine hydrochloride which had been formed. The precipitate was washed with toluene and the filtrate was freed from toluene in vacuo. This gave a residue of 40 g. The resulting product had an acid number of 49. It was a crude product. The yield was 97% of theory. $C_{11}H_{16}O_4P_2$ (274)

EXAMPLE 5

Reaction of methyl-vinylphosphinoyl chloride with cyclohexane-1,4-diol 23.2 g (0.2 mol) of cyclohexane-1,4-diol were added, together with 40.5 g (0.4 mol) of triethylamine, to 90 ml of toluene. To this were added dropwise with vigorous stirring 49.8 g (0.4 mol) of methyl-vinylphosphinoyl chloride at 20° C. with cooling. After subsequent stirring, the triethylamine hydrochloride which had been formed was filtered off under suction. The precipitate was washed with toluene and the filtrate was freed from toluene by distillation in vacuo. This residue crystallized. The product was isolated by digestion with methyl ethyl ketone. Melting point: 80° to 82° C. $C_{12}H_{22}O_4P_2$ (292)

| Calc.: | 49.32% C | 7.53% H | 21.23% P |
|---|---|---|---|
| Found: | 48.52% C | 8.02% H | 21.0% P |

EXAMPLE 6

Reaction of methyl-vinylphosphinoyl chloride with triethylene glycol 37.6 g (0.25 mol) of triethylene glycol were added, together with 50.6 g (0.5 mol) of triethylamine, to 100 ml of toluene. To this were added dropwise with vigorous stirring 62.25 g (0.5 mol) of methyl-vinylphosphinoyl chloride at 20° C. with cooling. After subsequent stirring, the triethylamine hydrochloride which had been formed was filtered off under suction. The precipitate was washed with toluene and the filtrate was freed from toluene by distillation in vacuo. This residue was distilled at 0.027 kPa and at a bath temperature of 240° to 245° C. via a thin-film evaporator. This gave 65 g. $n_D^{20}$: 1.4843. The yield was 80% of theory. $C_{12}H_{24}O_6P_2$ (326)

| Calc.: | 44.17% C | 7.36% H | 19.02% P |
|---|---|---|---|
| Found: | 44.4% C | 7.4% H | 18.8% P |

EXAMPLE 7 (ISOMER MIXTURE)

Reaction of methyl-vinylphosphinoyl chloride with dipropylene glycol (isomer mixture)

33.6 g (0.25 mol) of dipropylene glycol (isomer mixture) were added, together with 50.6 g (0.5 mol) of triethylamine, to 100 ml of toluene. To this were added dropwise with vigorous stirring 62.25 g (0.5 mol) of methyl-vinylphosphinoyl chloride over a period of 1.5 hours at 20° C. with cooling. Stirring was subsequently carried on for 18 hours. The triethylamine hydrochloride which had been formed was filtered off under suction. The precipitate was washed with toluene and the filtrate was freed from toluene by distillation in vacuo. This gave 77.5 g of crude product. $n_D^{20}$1.4768.

It was possible to purify the crude product by distillation with the aid of a thin-film evaporator at a bath temperature of about 220° C. and at 0.027 kPa. The yield was 100% of theory. $C_{12}H_{24}O_5P_2$ (310)

| Calc.: | 46.45% C | 7.74% H | 20.00% P |
|---|---|---|---|
| Found: | 46.4% C | 7.7% H | 19.8% P |

EXAMPLE 8

Reaction of ethyl vinylchlorophosphonate with 1,6-hexanediol 28.6 g (0.242 mol) of 1,6-hexanediol were added, together with 49 g (0.484 mol) of triethylamine, to 100 ml of toluene. To this were added dropwise with vigorous stirring 74.9 g (0.484 mol) of ethyl methylvinylchlorophosphonate at 20° C. with cooling. After subsequent stirring, the triethylamine hydrochloride which had been formed was filtered off under suction. The precipitate was washed with toluene and the filtrate was freed from toluene by distillation in vacuo. This gave 84 g. It was possible to purify the crude product by distillation with the aid of a thin-film evaporator at a bath temperature of 250° to 260° C. and at 0.04 kPa. $n_D^{20}$1.4623. The yield was 98% of theory. $C_{14}H_{28}O_6P_2$ (354)

| Calc.: | 47.46% C | 7.91% H | 17.52% P |
|---|---|---|---|
| Found: | 47.4% C | 7.8% H | 17.4% P |

EXAMPLE 9

Reaction of methyl-vinylphosphinoyl chloride with glycerol 9.2 g (0.1 mol) of glycerol were added, together with 30.4 g (0.3 mol) of triethylamine, to 70 ml of acetonitrile. To this were added dropwise with vigorous stirring 37.4 g (0.3 mol) of methyl-vinylphosphinoyl chloride over a period of 45 minutes at 20° to 25° C. with cooling. Stirring was then continued for 20 hours and then the triethylamine hydrochloride which had been formed was filtered off under suction. The precipitate was washed with ice cold acetonitrile and the filtrate was freed from acetonitrile by distillation in vacuo. This gave 43.5 g which was again filtered through a sinter under suction to remove residual amounts of triethylamine hydrochloride. The filtrate was the crude product. It had an acid number of 140. $n_D^{20}$ 1.4802.

It was possible to distil the crude product via a thin-film evaporator at a bath temperature of 240° C. and at 0.107 kPa. $C_{12}H_{23}O_6P_3$ (356)

EXAMPLE 10

A polyethylene vessel which had been well insulated with foamed plastic material and having a capacity of 10 l is first charged with 5180 g of deionized water, then 1740 g of sodium bicarbonate are dispersed therein and 1985 g of acrylic acid metered in slowly so that excessive foaming of the reaction solution is avoided, this solution being cooled to a temperature of about 10°--8° C. Then, 15 g of the compound according to the invention prepared according to Example 4 and 10 g of sodium diisooctyl sulphosuccinate (Rewopol V 2133 from REWO, Steinau) are added. At a temperature of 1°-10° C., the initiators, a redox system composed of 4.4 g of potassium peroxodisulphate dissolved in 170 g of water, 2.2 g of 2,2,-azobisamidinopropane dihydrochloride dissolved in 120 g of water, and 6.0 g of sodium pyrosulphite dissolved in 120 g of water are successively added with thorough stirring. The reaction solution is then left to stand without stirring while in the course of polymerization, during which the temperature increases to about 85° C., a solid gel is produced. This gel is then mechanically comminuted, dried at temperatures of above 80° and ground.

The product described above was incorporated by a conventional method into a baby diaper and in this application had a particularly good liquid retention.

EXAMPLE 11

A 10 litre plastic vessel is initially charged with 4576 g of ice and 1978 g of acrylic acid and then 1642 g of 50% strength NaOH are metered in slowly and then 22 g of the compound according to the invention, prepared according to Example 2, dissolved in 100 g of water, and 10 g of Rewopol V 2133 are added. The reaction solution is brought to 20° C. and to this are then added the initiators, a redox system composed of 6 g of potassium peroxodisulphate dissolved in 170 g of water, and 0.2 g of ascorbic acid dissolved in 120 g of water, and the mixture is left to stand without stirring. The gel resulting from polymerization is then mechanically comminuted, dried at temperatures of above 80° C. and ground.

EXAMPLE 12

A 10 litre polyethylene vessel is initially charged with 5250 g of deionized water, 1988 g of acrylic acid and 12 g of the compound according to the invention, prepared according to Example 1. After bringing the reaction solution to 18°-20° C., the initiators, 6 g of potassium peroxodisulphate in 170 g of water and 0.2 g of ascorbic acid in 20 g of water are added in succession and the reaction mixture is left to stand in a well insulated state without stirring. The progress of the reaction brings about an increase in the temperature to about 90° C. and a solid gel is obtained. This is comminuted mechanically using an extruder into which 1555 g of 50% strength NaOH are continuously metered, partial evaporation of the water occurring. The flocculent polymer is then finally dried at temperatures of above 80° C. and ground.

EXAMPLE 13

A polyethylene vessel which has been well insulated with foamed plastic material and has a capacity of 10 l is initially charged with 5280 g of deionized water, into which 1740 g of sodium bicarbonate are then dispersed and 1985 g of acrylic acid are slowly metered in so that excessive foaming of the reaction solution is avoided, this solution being cooled to a temperature of about 10°-8° C. Then, 15 g of the compound according to the invention prepared according to Example 6 and 10 g of sodium diisooctyl sulphosuccinate (Rewopol V 2133 from REWO, Steinau) are added. At a temperature of 6°-8° C., the initiators, a redox system composed of 2.2 g of 2,2'-azobisamidinopropane dihydrochloride dissolved in 20 g of water, 4.4 g of potassium peroxodisulphate dissolved in 170 g of water, and 6 g of sodium pyrosulphite dissolved in 120 g of water are successively added with thorough stirring. The reaction solution is then left to stand without stirring, while owing to the progress of polymerization, during which the temperature increases to about 85° C., a solid gel is obtained. This gel is then comminuted mechanically, dried at temperatures of above 80° and ground.

EXAMPLE 14

A 700 ml Quickfit flask fitted with a wall-sweeping, U-shaped stirrer, a thermometer and a reflux condenser is initially charged with 300 ml of cyclohexane into which 2 g of the protective colloid, copolymerized from a polybutadiene oil and maleic anhydride, are then dissolved. The monomer solution together with the initiator are then introduced dropwise in the course of 10 minutes at 20°-25° C.

58.2 g of acrylic acid and 1.2 g of methacrylic acid are dissolved in 80 ml of distilled water and then this solution is brought to a pH of 5 to 5.5 by adding 49.8 g of 50% strength NaOH solution with ice cooling. Then 0.6 g of the compound according to the invention prepared according to Example 1 and 3 ml of 1% strength aqueous $(NH_4)_2S_2O_8$ solution are added.

The oil bath is then heated in the course of 50 minutes to a temperature of 80° C. which corresponds to an internal temperature of 71°-72° C. and the stirrer is operated at a speed of 180 rpm. The polymerization takes place in 75-90 minutes and stirring is continued for a further 60 minutes.

The reflux condenser is then exchanged for a water separator and increasing the temperature of the oil bath to 140° C. over a period of 90-95 minutes results in 100 ml of water being distilled off.

The resulting colourless cross-linked pearls are filtered off under suction through a G glass sinter, washed once with 100 ml of acetone and dried at 50°/200° Torr for 30 minutes.

The product described above was incorporated by a conventional method into a baby diaper and in this application had a particularly good liquid retention.

EXAMPLE 15

A 1 litre glass polymerization flask fitted with a stirrer, thermometer and reflux condenser is initially charged with 600 ml of hexane into which 98.9 g of acrylic acid and 1.1 g of the compound according to the invention prepared according to Example 9 are then dissolved. While introducing a gentle stream of $N_2$, the mixture is heated by means of an electrically heated water bath to 68° C. after which 1.0 g of dilauryl peroxide is added. The progress of polymerization brings about a significant amount of refluxing and the resulting polymer flocculates. The mixture is stirred for a further 3 hours under reflux and then the polymer is filtered off under suction and dried in a drying oven to constant weight. This gives 100 g of a white powder which can be used as an acidic thickener in cosmetic preparations.

Further examples of the preparation of polymers according to the invention in accordance with the Examples 10 to 15 described here are summarized in the following Table. The proportions given are percentages by weight relative to the total monomer content. The following abbreviations are used:

| AA: | acrylic acid |
| --- | --- |
| MAA: | methacrylic acid |
| CTA: | crotonic acid |
| VPA: | vinylphosphonic acid |
| VPE: | semi-ester of vinylphosphonic acid |
| AMPA: | 2-acrylamido-2-methyl-propanesulphonic acid |
| AMPP: | 2-acrylamido-2-methyl-propanephosphonic acid |
| AM: | acrylamide |

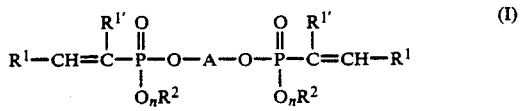

in which
$R^1$ and $R^{1'}$, independently of one another, are hydrogen or $(C_1-C_4)$-alkyl,
$R^2$ is $(C_1-C_4)$-alkyl,
n is 0 or 1 and
A is straight-chain or branched $(C_2-C_{12})$-alkylene or a group of the formula II

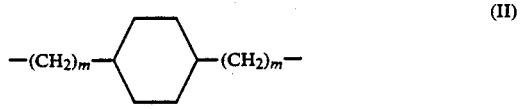

in which m is 0 or 1, or a group of the formula III

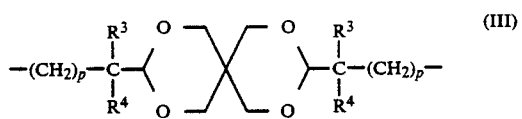

in which $R^3$ and $R^4$, independently of one another, are $(C_1-C_4)$alkyl and p is 0 or 1, or a group of the formula IV

in which x is 1 to 12 or a group of the formula V

in which x is 1 to 12 or a group of the formula VI

TABLE

| Exple. | Prepared according to Example | AA % | MAA % | AMPA % | AMPP % | VPA % | VPE % | CTA % | AM % | Compound according to the invention from Example | % | Degree of neutralization % |
| --- | --- | --- | --- | --- | --- | --- | --- | --- | --- | --- | --- | --- |
| 16 | 13 | 79.25 | | 20.00 | | | | | | 1 | 0.75 | 75 |
| 17 | 11 | 98.50 | | | | | | | | 3 | 1.50 | 75 |
| 18 | 13 | 99.25 | | | | | | | | 8 | 0.75 | 75 |
| 19 | 13 | 99.25 | | | | | | | | 9 | 0.75 | 65 |
| 20 | 13 | 99.25 | | | | | | | | 5 | 0.75 | 65 |
| 21 | 14 | 80.0 | 10.0 | 9.5 | | | | | | 9 | 0.5 | 48 |
| 22 | 12 | 70.0 | | 25.0 | | 4.0 | | | | 2 | 1.0 | 75 |
| 23 | 12 | 75.0 | | 20.0 | | | 4.0 | | | 3 | 1.0 | 75 |
| 24 | 12 | 85.0 | 10.0 | | | | 4.0 | | | 7 | 1.0 | 70 |
| 25 | 13 | 40.0 | | 25.0 | 4.0 | | | | 30.0 | 6 | 1.0 | 80 |
| 26 | 13 | 75.0 | | 19.3 | | | | 5.0 | | 8 | 0.7 | 55 |
| 27 | 13 | 95.0 | | | 4.6 | | | | | 8 | 0.4 | 45 |
| 28 | 13 | 85.0 | | 10 | 4.5 | | | | | 8 | 0.5 | 70 |
| 29 | 12 | 97.4 | | | | | | | | 8 | 2.6 | 80 |
| 30 | 13 | | 99.4 | | | | | | | 9 | 0.60 | 85 |

We claim:

1. Water-swellable hydrogel prepared by copolymerization of ethylenically unsaturated hydrophilic monomers, characterized in that the compounds of the formula I in which B represents straight-chain or branched $(C_3-C_{12})$-alkylene and $R^1$, $R^{1'}$, $R^2$ and n are as defined above, are employed as cross-linking agents during the copolymerization.

2. Water-swellable hydrogel according to claim 1, characterized in that the hydrophilic monomers used in the copolymerization are acrylic acid, methacrylic acid, crotonic acid, 2-acrylamido-2-methylpropane-sulphonic acid and -phosphonic acid, vinylphosphonic acid, semi-esters of vinylphosphonic acid, salts thereof, acrylamide, N-vinylamides, or mixtures thereof.

3. Water-swellable hydrogel according to claim 2, characterized in that the hydrophilic monomer used in the copolymerization is acrylic acid or salts thereof or both.

4. Water-swellable hydrogel comprising units derived from hydrophilic monomers and compounds of formula I in claim 1 as cross-linking agents.

* * * * *